United States Patent [19]

Wommack, Jr.

[11] 4,018,926

[45] Apr. 19, 1977

[54] ALKYL 4-[O-(SUBSTITUTED METHYLENEAMINO)-PHENYL]-3-THIOALLOPHANATE MITICIDES AND FUNGICIDES

[75] Inventor: Joel Benjamin Wommack, Jr., Wilmington, Del.

[73] Assignee: E. I. Du Pont de Nemours and Company, Wilmington, Del.

[22] Filed: Jan. 13, 1976

[21] Appl. No.: 648,760

Related U.S. Application Data

[60] Division of Ser. No. 473,156, May 24, 1974, Pat. No. 3,958,007, and a continuation-in-part of Ser. No. 865,947, Oct. 13, 1969, Pat. No. 3,836,569.

[52] U.S. Cl. .............................. 424/258; 424/245; 424/248.5; 424/263; 424/275; 424/285; 424/287; 424/289; 424/294; 424/300

[51] Int. Cl.[2] .......................................... A01N 9/22

[58] Field of Search .......... 424/245, 248, 263, 275, 424/285, 287, 289, 294, 300, 258

[56] References Cited

UNITED STATES PATENTS

| | | | |
|---|---|---|---|
| 3,745,187 | 7/1973 | Noguchi et al. | 260/455 A |
| 3,836,569 | 9/1974 | Wommack | 260/470 |
| 3,860,586 | 1/1975 | Kilbourn et al. | 260/240 G |
| 3,958,007 | 5/1976 | Wommack | 424/300 |

*Primary Examiner*—Leonard Schenkman

[57] ABSTRACT

Various alkyl 4-[o-(substituted methyleneamino)-phenyl]3-thioallophanates are useful as fungicides and mite ovicides.

The compounds are prepared by reacting alkyl 4-(o-aminophenyl)-3-thioallophanates with aldehydes or trialkyl orthoformates. Some of the compounds are prepared by further reacting the reaction product of an alkyl 4-(o-aminophenyl)-3-thioallophanate and a trialkyl orthoformate with a primary or secondary amine.

Exemplary species are methyl 4-[o-(o-fluorobenzylideneamino)phenyl]-3-thioallophanate, methyl 4-[o-(4-methylbenzylideneamino)phenyl]-3-thioallophanate and methyl 4-[o-(2-furfurylideneamino)phenyl]-3-thioallophanate.

14 Claims, No Drawings

ALKYL 4-[O-(SUBSTITUTED METHYLENEAMINO)-PHENYL]-3-THIOALLOPHANATE MITICIDES AND FUNGICIDES

CROSS REFERENCE TO RELATED APPLICATION

This is a divisional of my copending application Ser. No. 473,156, filed May 24, 1974, now U.S. Pat. No. 3,958,007 which is a continuation-in-part of my copending application Ser. No. 865,947, filed Oct. 13, 1969, now U.S. 3,836,569.

BACKGROUND OF THE INVENTION

This invention relates to a group of alkyl 4-[o-(substituted methyleneamino)phenyl]3-thioallophanates and to methods of using these compounds to prevent or mitigate damage to plants and inanimate organic materials by fungi and mites.

The survival of man has for a long time been dependent in a large measure upon his ability to protect from the various agents of destruction, plants and their products which satisfy his basic needs. With the rapidly increasing population of the world, it becomes imperative that there be continuing great improvements in the efficiency of the materials and the methods employed to provide this protection. These improvements can be in the form of effective control of more kinds of pests or in the form of requiring less material or work. The materials and methods of this invention represent marked advances in both of these possible areas of improvement, as will be explained more fully.

It has been discovered that application of the compounds of this invention by the methods of this invention entirely precludes or reduces damage to plants and inanimate organic materials due to fungi and mites. Fungus mycelia are killed or prevented from developing further by the presence of one or more of the compounds, i.e., the compounds are fungicidal or fungistatic. The compounds further prevent mite populations from expanding or reduce them to a low level or even eliminate them by preventing the normal hatching of their eggs, i.e., the compounds are mite ovicides.

SUMMARY OF THE INVENTION

It has found that the above outstanding fungicidal activity can be obtained by applying to the locus of fungus infestation, the compounds represented by the following formula:

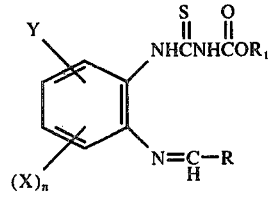

wherein

X is hydrogen, fluorine, chlorine, or bromine;

Y is hydrogen or alkyl of 1 to 4 carbon atoms;

$R_1$ is alkyl of 1 to 12 carbon atoms;

R is phenyl; thienyl; furyl; naphthyl; pyridyl; quinolyl; phenyl substituted with halogen, alkyl, nitro, hydroxy, and alkoxy; alkyl of 1 to 12 carbon atoms; alkoxy of 1 to 3 carbon atoms or

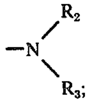

$R_2$ is hydrogen or alkyl of 1 to 4 carbon atoms;

$R_3$ is alkyl of 1 to 4 carbon atoms, provided that $R_2$ and $R_3$ can be taken together and be $-CH_2CH_2OCH_2CH_2-$ or $-(CH_2)_m-$; when Y is alkyl, *n* is O; when Y is hydrogen, *n* is 1, 2 or 3; *m* is 4 to 6; and the sodium, potassium, lithium, calcium, barium, copper, zinc and manganese salts of these compounds.

When the expression "phenyl substituted with halogen, alkyl, nitro, hydroxy, and alkoxy" is used in the disclosure and claims, it is to be understood that this is intended to cover mono, di, and tri substituted phenyl radicals. These mono, di and tri substituted compounds are within the scope of the invention and have been exemplified in the examples.

Preferred are those compounds where X and Y are hydrogen and $R_1$ is methyl, ethyl or isopropyl.

Particularly preferred because of their activity are the compounds methyl 4-[o-fluorobenzylideneamino)-phenyl]-3-thioallophanate, methyl 4-[o-(4-methylbenzylideneamino)phenyl]-3-thioallophanate, and methyl 4-[o-(2-bromobenzylideneamino)-phenyl]-3-thioallophanate.

DETAILED DESCRIPTION OF THE INVENTION

The compounds of the invention can be prepared by the following methods.

The compounds of Formula I below are prepared by reacting alkyl 4-(o-aminophenyl)-3-thioallophanates with aldehydes in the presence of p-toluene sulfonic acid in a suitable solvent such as benzene according to the equation:

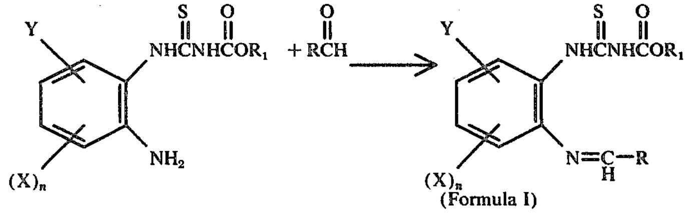

(Formula I)

The compounds of Formula II below are prepared by reacting allyl 4-(o-aminophenyl)-3-thioallophanates with trialkyl orthoformates according to the equation:

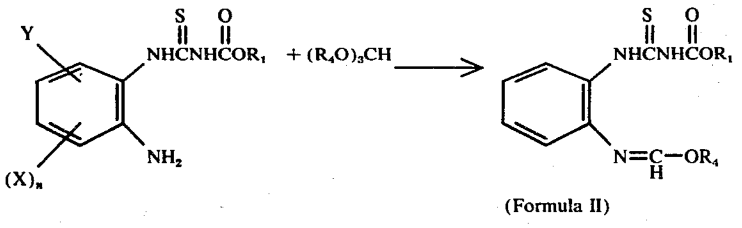

(Formula II)

The compounds of Formula III below are prepared by reacting Formula II type compounds with the appropriate primary or secondary amine according to the equation:

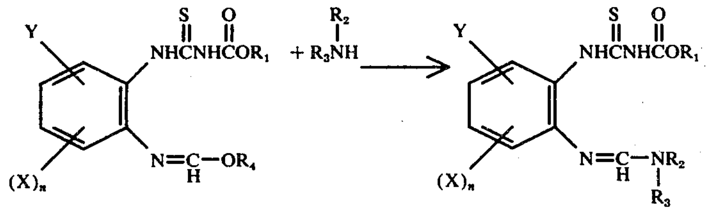

(Formula III)

In the above equations R, $R_1$, $R_2$, $R_3$, X and Y are as previously defined and $R_4$ is alkyl of 1 to 3 carbon atoms.

The alkali metal salts of type I, II and III are prepared by treating the appropriate compound with the appropriate alkali metal methoxide, prepared from the appropriate metal and methanol. The salts are isolated by diluting the methanol solution with ether and filtering, or by stripping off the solvent.

Other metal salts of compounds of types I, II and III are prepared by treating the sodium salts of these compounds, prepared from sodium methoxide in methanol, with an aqueous solution of the appropriate inorganic metal salt such as calcium chloride, barium sulfate, cupric sulfate, zinc chloride or maganese sulfate.

Methods for preparing the alkyl 4-(o-aminophenyl)-3-thioallophanates are disclosed in application Ser. No. 865,964, filed Oct. 13, 1969 by Charles D. Adams entitled "Alkyl 4-(o-aminophenyl)-3-thioallophanates as Fungicides". In general those intermediate compounds are prepared by reacting an o-phenylenediamine with the appropriate alkoxycarbonyl isothiocyanate. The alkoxycarbonyl isothiocyanates can be prepared as described in Bull. Chem. Soc. (Japan) 36, 1214.

Alternatively, alkyl 4-(o-aminophenyl)-3-thioallophanates are prepared by dissolving alkoxycarbonylisothiocyanate in benzene and adding the solution to o-phenylenediamine in benzene at 10°–15° C. After stirring for one hour at room temperature, the alkyl 4-(o-aminophenyl)-3-thioallophanate is isolated by filtration.

The general method of preparation of the compounds of this invention is illustrated by the following examples, the amounts being given as parts by weight unless otherwise specified.

EXAMPLE 1

Methyl 4-(o-benzylideneaminophenyl)-3-thioallophanate.

Methyl 4-(o-aminophenyl)-3-thioallophanate is prepared by dissolving 11.7 parts of methoxycarbonyl isothiocyanate in 50 parts of benzene and adding this to 10.8 parts of o-phenylenediamine in 200 parts of benzene at 10°–15° C. After stirring for 1 hour at room temperature, 13.7 parts of methyl 4-(aminophenyl)-3-thioallophanate is recovered by filtration, m.p. 187° C.(D).

Nine parts of the methyl 4-(o-aminophenyl)-3-thioallophanate with 0.5 parts of p-toluenesulfonic acid and 4.5 parts of benzaldehyde are suspended in 300 parts of benzene. This mixture is heated at reflux for one hour during which time 100 parts of benzene are removed by distillation. After the hot solution is filtered and cooled, 13 parts of methyl 4-(o-benzylideneaminophenyl)-3-thioallophanate are obtained from the filtrate as an off white solid, m.p. 142–144μC. The melting point is raised to 145–147.5μC. after recrystallization from acetonitrile.

EXAMPLE 2

The following compounds (C) can be synthesized by the method of Example 1 substituting the appropriate alkyl 4-(o-aminophenyl)-3-thioallophanate (A) for methyl 4-(o-aminophenyl)-3-thioallophanate and the appropriate aldehyde (B) for benzaldehyde.

COMPOUND 1

A. Methyl 4-(o-aminophenyl)-3-thioallophanate
B. 2-Thiophenecarboxyaldehyde
C. Methyl 4-[o-(2-thenylideneamine)phenyl]-3-thioallophanate

COMPOUND 2

A. Methyl 4-(o-aminophenyl)-3-thioallophanate
B. Furfural
C. Methyl 4-[o-(2-furfurylideneamino)phenyl]-3-thioallophanate, melting point 142°–145° C.(D).

COMPOUND 3

A. Methyl 4-(o-aminophenyl)-3-thioallophanate

B. 1-Naphthaldehyde
C. Methyl 4- o-(1-naphthylideneamino)phenyl]-3-thioallophanate

COMPOUND 4

Methyl 4-(o-aminophenyl)-3-thioallophanate
B. Pyridine-2-carboxyaldehyde
C. Methyl 4-[o-(2-pyridylmethyleneamino)phenyl]-3-thioallophanate, m.p. 155°–160° C.(D).

COMPOUND 5

A. Methyl 4-(o-aminophenyl)-3-thioallophanate
B. Quinoline-2-carboxaldehyde
C. Methyl 4-[o-(2-quinolylmethyleneamino)phenyl]-3-thiolallophanate m.p. 182°–183° C.(D).

COMPOUND 6

A. Methyl 4-(o-aminophenyl)-3-thioallophanate
B. o-chlorobenzaldehyde
C. Methyl 4-[o-(o-chlorobenzylideneamino)phenyl]-3-thioallophanate, m.p. 170°–171° C.

COMPOUND 7

A. Methyl 4-(o-aminophenyl)-3-thioallophanate
B. o-fluorobenzaldehyde
C. Methyl 4-[o-(o-fluorobenzylideneamino)phenyl]-3-thioallophanate, m.p. 158°–159° C.

COMPOUND 8

A. Methyl 4-(o-aminophenyl)-3-thioallophanate
B. 2,4-Dichlorobenzaldehyde
C. Methyl 4-[o-(2,4-dichlorobenzylideneamino)-phenyl]-3-thioallophanate, m.p. 187°–188° C.

COMPOUND 9

A. Methyl 4-(o-aminophenyl)-3-thioallophanate
B. p-Tolualdehyde
C. Methyl 4-[o-(4-methylbenzylideneamino)-phenyl]-3-thioallophanate, m.p. 153°–154.5° C.

COMPOUND 10

A. Methyl 4-(o-aminophenyl)-3-thioallophanate
B. o-Tolualdehyde
C. Methyl 4-[o-(2-methylbenzylideneamino)-phenyl]-3-thioallophanate, m.p. 151°–155° C.

COMPOUND 11

A. Methyl 4-(o-aminophenyl)-3-thioallophanate
B. o-Nitrobenzaldehyde
C. Methyl 4-[o-(2-nitrobenzylideneamino)phenyl]-3-thioallophanate, m.p. 195°–196° C.(D).

COMPOUND 12

A. Methyl 4-(o-aminophenyl)-3-thioallophanate
B. M-Nitrobenzaldehyde
C. Methyl 4-[o-(3-nitrobenzylideneamino)phenyl]-3-thioallophanate, m.p. 194°–195° C.(D).

COMPOUND 13

A. Methyl 4-(o-aminophenyl)-3-thioallophanate
B. p-Anisaldehyde
C. Methyl 4-[o-(4-methoxybenzylideneamino)-phenyl]-3-thioallophanate, m.p. 158°–160° C.

COMPOUND 14

A. Methyl 4-(o-aminophenyl)-3-thioallophanate
B. p-Isopropylbenzaldehyde
C. Methyl 4-(o-(4-isopropylbenzylideneamino)-phenyl]-3-thioallophanate, m.p. 141°–142° C.

COMPOUND 15

A. Methyl 4-(o-aminophenyl)-3-thioallophanate
B. m-Fluorobenzaldehyde
C. Methyl 4-[o-(3-fluorobenzylideneamino)phenyl]-3-thioallophanate, m.p. 162°–163.5° C.

COMPOUND 16

A. Methyl 4-(o-aminophenyl)-3-thioallophanate
B. p-fluorobenzaldehyde
C. Methyl 4-[o-(4-fluorobenzylideneamino)phenyl]-3-thioallophanate, m.p. 163°–164.5° C.

COMPOUND 17

A. Methyl 4-(o-aminophenyl)-3-thioallophanate
B. Acetaldehyde
C. Methyl 4-(o-ethylideneaminophenyl)-3-thioallophanate

COMPOUND 18

A. Methyl 4-(o-aminophenyl)-3-thioallophanate
B. Pivaldehyde
C. Methyl 4-[o-(2,2-dimethylpropylideneamino)-phenyl]-3-thioallophanate, m.p. 152°–155° C.

COMPOUND 19

A. Methyl 4-(o-aminophenyl)-3-thioallophanate
B. Tridecenal
C. Methyl 4-(o-tridecylideneaminophenyl)-3-thioallophanate

COMPOUND 20

A. Methyl 4-(2-amino-4-chlorophenyl)-3-thioallophanate
B. o-Fluorobenzaldehyde
C. Methyl 4[4-chloro-2-(2-fluorobenzylideneamino)phenyl]-3-thioallophanate

COMPOUND 21

A. Methyl 4-(2-amino-4-fluorophenyl)-3-thioallophanate
B. o-Fluorobenzaldehyde
C. Methyl 4-[4-fluoro-2-(2-fluorobenzylideneamino)phenyl]-3-thioallophanate

COMPOUND 22

A. Methyl 4-(2-amino-4-bromophenyl)-3-thioallophanate
B. Benzaldehyde
C. Methyl 4-[4-bromo-2-(benzylideneamino)-phenyl]-3-thioallophanate

COMPOUND 23

A. Methyl 4-(2-amino-4-methylphenyl)-3-thioallophanate
B. Benzaldehyde
C. Methyl 4-[2-(benzylideneamino)-4-methylphenyl]-3-thioallophanate

COMPOUND 24

A. Methyl 4-(2-amino-4-butylphenyl)-3-thioallophanate
B. Benzaldehyde
C. Methyl 4-[2-(benzylideneamino)-4-butylphenyl]-3-thioallophanate

COMPOUND 25

A. Methyl 4-[2-amino-4,5-dichlorophenyl]-3-thioallophanate
B. Benzaldehyde
C. Methyl 4-[2-(benzylideneamino)-4,5-dichlorophenyl]-2-thiophanate

COMPOUND 26

A. n-Amyl 4-(o-aminophenyl)-3-thioallophanate
B. Benzaldehyde
C. N-Amyl 4-(o-benzylideneaminophenyl)-3-thioallophanate Compound 27

A. Dodecyl 4-(o-aminophenyl)-3-thioallophanate
B. Benzaldehyde
C. Dodecyl 4-(o-benzylideneaminophenyl)-3-thioallophanate.

Compound 28

A. Methyl 4-(o-aminophenyl)-3-thioallophanate
B. 3,4-Dihydroxybenzaldehyde
C. Methyl 4-[o-(3,4-dihydroxybenzylideneamino)-phenyl]-3-thio-allophanate, m.p. 175°–181° C. (D).

Compound 29

A. Methyl 4-(o-aminophenyl)-3-thioallophanate
B. Salicylaldehyde
C. Methyl 4-[o-(o-hydroxybenzylideneamino)-phenyl]-3-thioallo-phanate, m.p. 178°–179° C.(D).

Compound 30

A. Methyl 4-(o-aminophenyl)-3-thioallophanate
B. 2,4,6-Trihydroxybenzaldehyde
C. Methyl 4-[o-(2,4,6-trihydroxybenzylideneamino)-phenyl]-3-thioallophanate Compound 31

A. Methyl 4-(o-aminophenyl)-3-thioallophanate
B. 2,4-Dimethylbenzaldehyde
C. Methyl 4-[o-(2,4-dimethylbenzylideneamino)-phenyl]-3-thioallophanate Compound 32

A. Methyl 4-(o-aminophenyl)-3-thioallophanate
B. 2,4,6-Trimethylbenzaldehyde
C. Methyl 4-[o-(2,4,6-trimethylbenzylideneamino)-phenyl]-3-thioallophanate Compound 33

A. Methyl 4-(o-aminophenyl)-3-thioallophanate
B. 2,6-Dichlorobenzaldehyde
C. Methyl 4-[o-(2,6-dichlorobenzylideneamino)-phenyl]-3-thioallophanate, m.p. 175°–177° C.(D).

Compound 34

A. Methyl 4-(o-aminophenyl)-3-thioallophanate
B. 2,4,5-Trichlorobenzaldehyde
C. Methyl 4-[o-(2,4,5-trichlorobenzylideneamino)-phenyl]-3-thioallophanate Compound 35

A. Methyl 4-(o-aminophenyl)-3-thioallophanate
B. 2,4-Dinitrobenzaldehyde
C. Methyl 4-[o-(2,4-dinitrobenzylideneamino)-phenyl]-3-thioallophanate Compound 36

A. Methyl 4-(o-aminophenyl)-3-thioallophanate
B. 2,4,6-Trinitrobenzaldehyde
C. Methyl 4-[o-(2,4,6-trinitrobenzylideneamino)-phenyl]-3-thioallophanate Compound 37

A. Methyl 4-(o-aminophenyl)-3-thioallophanate
B. 3,4-Dimethoxybenzaldehyde
C. Methyl 4-[o-(3,4-dimethoxybenzylideneamino)-phenyl]-3-thioallophanate Compound 38

A. Methyl 4-(o-aminophenyl)-3-thioallophanate
B. 2,4,6-Trimethoxybenzaldehyde
C. Methyl 4-[o-(2,4,6-trimethoxybenzylideneamino)phenyl]-3-thioallophanate Compound 39

A. Methyl 4-(o-aminophenyl)-3-thioallophanate
B. m-tolualdehyde
C. Methyl 4-[o-(3-methylbenzylideneamino)-phenyl]-3-thioallophanate, m.p. 162°–163.5° C.

Compound 40

A. Methyl 4-(o-aminophenyl)-3-thioallophanate
B. p-Nitrobenzaldehyde
C. Methyl 4-[o-(4-nitrobenzylideneamino)phenyl]-3-thioallophanate, m.p. 191.5° – 193° C.

Compound 41

A. Methyl 4-(o-aminophenyl)-3-thioallophanate
B. 4-Chlorobenzaldehyde
C. Methyl 4-[o-(4-chlorobenzylideneamino)phenyl]-3-thioallophanate, m.p. 182°–183.5° C.

Compound 42

A. Methyl 4-(o-aminophenyl)-3-thioallophanate
B. o-Anisaldehyde
C. Methyl 4-[o-(2-methoxybenzylideneamino)-phenyl]-3-thio-allophanate, m.p. 152°–154° C.

Compound 43

A. Methyl 4-(o-aminophenyl)-3-thioallophanate
B. m-Anisaldehyde
C. Methyl 4-[o-(3-methoxybenzylideneamino)-phenyl]-3-thioallophanate Compound 44

A. Methyl 4-(o-aminophenyl)-3-thioallophanate
B. 2-Bromobenzaldehyde
C. Methyl 4-[o-(2-bromobenzylideneamino)phenyl]-3-thio-allophanate, m.p. 173°–175° C.

Compound 45

A. Methyl 4-(o-aminophenyl)-3-thioallophanate
B. 3-Bromobenzaldehyde
C. Methyl 4-[o-(3-bromobenzylideneamino)phenyl]-3-thio-allophanate, m.p. 161°–163° C.

Compound 46

A. Methyl 4-(o-aminophenyl)-3-thioallophanate
B. 4-Bromobenzaldehyde
C. Methyl 4-[o-(4-bromobenzylideneamino)phenyl]-3-thioallophanate, m.p. 190.5°–192° C.

Example 3

1.9 Parts of methyl 4-(o-aminophenyl)-3-thioallophanate in 200 parts of benzene are treated with 5 parts of trimethyl orthoformate. This mixture is refluxed for 2 hours and the solvent is removed yielding 1.5 parts of methyl 4-[o-methoxymethyleneaminophenyl]-3-thioallophanate as a white solid, m.p. 128°–130° C.

Example 4

Methyl 4-(o-propoxymethyleneaminophenyl)-3-thioallophanate is prepared in the same manner as methyl 4-[o-methoxymethyleneaminophenyl)-3-thioallophanate from methyl 4-(o-aminophenyl)-3-thioallophanate substituting tri-n-propyl orthoformate for trimethyl orthoformate.

EXAMPLE 5

Ten parts of methyl 4-[o-methoxymethyleneaminophenyl]-3-thioallophanate (prepared as described in Example 3) in 200 parts of benzene is treated with 20 parts of dimethylamine. After standing several hours this solution is evaporated yielding methyl 4-[o-dimethylaminomethyleneaminophenyl]-3-thioallophanate.

EXAMPLE 6

The following compounds (C) can be synthesized by the method of Example 5 substituting the appropriate alkyl 4-(o-methoxymethyleneaminophenyl)-3-thioallophanate (A) for methyl 4-(o-methoxymethyleneaminophenyl)-3-thioallophanate and the appropriate amine (B) for dimethylamine.

Compound 1

A. Methyl 4-(o-methoxymethyleneaminophenyl)-3-thioallophanate
B. Methylamine
C. Methyl 4-(o-methylaminomethyleneaminophenyl)-3-thioallophanate Compound 2

A. Ethyl 4-(o-methoxymethyleneaminophenyl)-3-thioallophanate
B. n-Butylamine
C. Ethyl 4-(o-butylaminomethyleneaminophenyl)-3-thioallophanate Compound 3

A. Methyl 4-(o-methoxymethyleneaminophenyl)-3-thioallophanate
B. Morpholine
C. Methyl 4-(o-morpholinomethyleneaminophenyl)-3-thioallophanate Compound 4

A. Methyl 4-(o-methoxymethyleneaminophenyl)-3-thioallophanate
B. Pyrrolidine
C. Methyl 4-[o-pyrrolidinomethyleneaminophenyl)-3-thioallophanate Compound 5

A. Methyl 4-(o-methoxymethyleneaminophenyl)-3-thioallophanate
B. Hexamethyleneimine
C. Methyl 4-[o-hexamethyleneiminomethyleneaminophenyl)-3-thioallophanate

EXAMPLE 7

3.13 Parts of methyl 4-(o-benzylideneaminophenyl)-3-thioallophanate are dissolved in 50 parts of a 5% sodium methoxidemethanol solution and this solution is diluted with ether precipitating the sodium salt of methyl 4-(o-benzylideneaminophenyl)-3-thioallophanate which is removed by filtration.

EXAMPLE 8

The following compounds (C) can be prepared by the method of Example 7 by substituting the required alkoxide (B), prepared from the appropriate alkali metal and methanol, for sodium methoxide.

Compound 1

A. Methyl 4-(o-benzylideneaminophenyl)-3-thioallophanate
B. Lithium methoxide
C. Methyl 4-(o-benzylideneaminophenyl)-3-thioallophanate, lithium salt Compound 2

A. Methyl 4-(o-benzylideneaminophenyl)-3-thioallophanate
B. Potassium ethoxide
C. Methyl 4-(o-benzylideneaminophenyl)-3-thioallophanate, potassium salt Example 9

3.13 Parts of methyl 4-(o-benzylideneaminophenyl)-3-thioallophanate is dissolved in 50 parts of a 5% solution of sodium ethoxide-methanol. 1.47 Parts of calcium chloride dihydrate dissolved in 30 parts of water are added to the methanol solution. The white calcium salt of methyl 4-(o-benzylideneaminophenyl)-3-thioallophanate is removed by filtration, m.p. >250° C.

EXAMPLE 10

The following salts (C) can be synthesized by the method of Example 9 by substituting the appropriate inorganic metal salt (B) for the calcium chloride dihydrate.

Compound 1

A. Methyl 4-(o-benzylideneaminophenyl)-3-thioallophanate
B. Barium chloride
C. Methyl 4-(o-benzylideneaminophenyl)-3-thioallophanate, barium salt Compound 2

A. Methyl 4-(o-benzylideneaminophenyl)-3-thioallophanate
B. Cupric sulfate pentahydrate.
C. Methyl 4-(o-benzylideneaminophenyl)-3-thioallophanate,
cupric salt, m.p. >300° C.

Compound 3

A. Methyl 4-(o-benzylideneaminophenyl)-3-thioallophanate
B. Zinc chloride
C. Methyl 4-(o-benzylideneaminophenyl)-3-thioallophanate, zinc salt Compound 4

A. Methyl 4-(o-benzylideneaminophenyl)-3-thioallophanate

B. Manganese sulfate

C. Methyl 4-(o-benzylideneaminophenyl)-3-thioallophanate, manganese salt

As mentioned previously, it has been found that the compounds of the invention posses outstanding fungicidal and mite ovicidal activity when employed to prevent or mitigate damage to plants and inanimate organic materials. The paragraphs which follow describe in more detail the utility of this invention.

The compounds of the invention control a wide variety of fungus diseases of foliage, fruit, stems and roots of growing plants without damage to the host. Fruits, tubers, bulbs, roots, seeds and other plant parts harvested for food, animal feed or for other purposes are protected from fungus deterioration during processing, distribution and storage. Seeds, tubers, cuttings and other plant propagation materials are protected from fungus attack during handling and storage, as well as in the soil after planting. Wood, fabric, fiber board, paper and other industrial materials are protected from unsightly stain and destructive decay caused by fungi. Luggage, shoes, shower curtains, carpets, mats, clothing and other useful household, public or industrial items are protected from rot, fungus stains and mold growth. Painted surfaces are protected from stain and discoloration by incorporation of a compound of this invention in the paint formulation.

The many fungi against which the compounds of this invention are active may be represented by, but is not intended to be limited to, the following: *Venturia inaequalis*, which causes apple scab; *Podosphaera leucotricha*, which causes powdery mildew on apple; *Uromyces phaseoli*, which causes bean rust; *Cercospora apii*, which causes early blight of celery; *Cercospora beticola*, which causes leaf spot of sugar beets; *Sclerotinia sclerotiorum*, which causes rot of vegetable crops, such as lettuce, beans, carrots, and celery; *Colletotrichum spp.*, which cause anthracnose of fruits and vegetables, such as beans, tomatoes and coffee; *Septoria apii*, which causes late blight of celery; *Mycosphaerella musicola*, which causes Sigotoka disease of banana; *Piricularia sp.*, which causes Johnson spot on banana; *Erysiphe cichoracearum* which causes powdery mildew on cantaloupe and other cucurbit crops; *Penicillium digitatum*, Phomopsis spp., and *Diplodia natalensis*, which cause fruit rots on citrus; *Ceratostomella ulmi*, which causes Dutch elm disease; *Sphaerotheca humuli*, which causes powdery mildew on roses; *Diplocarpon rosae*, which causes black spot on roses; *Ramularia sp.*, which causes leaf spots on ornamental plants; *Botrytis cinerea*, which causes blossom and fruit rots of ornamentals, fruits and vegetables; *Uncinula necator*, which causes powdery mildew on grapes; *Guignardia bidwellii* which causes grape black rot; *Melonconium fuligineum*, which causes white rot of grapes; *Coccomyces hiemalis*, which causes cherry leaf spot; *Cytospora sp.*, which cause cankers of trees; *Cladosporium carpophilum*, which causes peach scab; *Fusicladium effusum*, which causes pecan scab; *Erysiphe graminis*, which causes powdery mildew on cereals; *Monolinia* (*Sclerotinia*) laxa and *M. fructicola*, which cause brown rot of stone fruits, such as peaches, cherries and apricots; *Pseudopeziza ribes*, which causes leaf spot on gooseberry; *Piricularia oryzae*, which causes rice blast; *Puccinia glumarum P. coronata* and *P. glumarum*, which cause leaf rusts of wheat, oats and grasses, respectively; *Puccinia graminis tritici*, which causes stem rust of wheat; *Claviceps purpurea*, which causes ergot of rye and grasses; *Aspergillus niger*, which causes cotton boll rot as well as decay following wounding in many plant tissues; *Aspergillus flavus*, which causes mold growth on peanuts, as well as on other food and field materials; *Aspergillus terreus*, which is common in soil and attacks vegetable matter; *Tilletia caries* and other *Tilletia species*, which cause common bunt of wheat; *Ustilago tritici*, *Ustilago nigra*, *Ustilago avena* (and other *Ustilago* species), which cause loose smut of wheat, barley, and oats, respectively; *Urocystis tritici* and other *Urocystis* species, which cause loose smut of wheat; *Sphacelotheca sorghi*, which causes covered smut of sorghum; *Ustilago hordei* and *Ustilago kolleri*, which cause covered smut of barley and oats, respectively; *Pithomyces chartorum*, which is present in turf, pastures, and other grassy areas and is known to have several secondary effects; *Gloeodes pomigena*, which causes sooty blotch on apples; *Physalospora obtusa*, which causes black rot on apples; *Microthyriella rubi*, which causes flyspeck on applies; various species of *Rhizoctonia*, *Fusarium* and *Verticillium* present in soil and attacking the roots or other underground parts and the vascular system of a variety of plants; various species of *Penicillium* growing on such things as fabric, fiber board, leather goods and paint; species of *Myrothecium attacking such items as shower curtains, carpets, mats and clothing.*

The mite ovicidal action of the compounds of this invention is useful in preventing the development of damaging populations of mites or in causing the gradual reduction of existing populations. The movement of mites is limited. Thus, an increase in population or the continuation of a high population in a particular locus depends largely upon the hatching of eggs laid in that locus.

Mite eggs do not hatch to produce living young if these eggs are treated with one of these compounds, or if they are laid on a surface containing one of these compounds. Further, the eggs will not hatch if they are laid by a female mite that has been in contact with one of these compounds, or are laid by a female mite that is ingesting or has recently ingested food such as plant juices containing one of these compounds. This interference with the hatching of eggs prevents the population from increasing significantly beyond that present at the time of treatment. Also, this ovidical action, along with the high natural mortality of adults, can largely eliminate mites from an already infested area over a relatively short period of time. Further as long as the compounds are present on the surface the mites occupy or remain in their food supply, new populations cannot develop.

Many species of mites which cause damage to fruits, field crops, vegetables, and ornamentals under a wide variety of circumstances, are controlled by the compounds and methods of this invention. The extent of the practical utility of the mite control obtained is represented by, but is not intended to be limited to, the following listing of specific susceptible mites along with the types of damage that they can cause: *Panonychus ulmi* (European red mite) and *Tetranychus telarius* (*two-spotted mite*) *which are commonly called "orchard mites"; these mites attack a great many deciduous tree fruits including apples, pears, cherries, plums and peaches; Tetranychus atlanticus* (Atlantic or strawberry mite), *T. cinnabarinus* (carmine spider mite) and T. pacificus (Pacific mite); these mites attack cotton and numerous other crop plants; Paratetranychus citri (citrus red mite) and others which attack citrus; *Bryobia praetiosa* (clover mite) which attacks clover, alfalfa and other crops; *Phyllocoptruta oleivora*, the citrus rust mite; *Aceria neocynodomis* which attacks grasses and other plants; *Tyrophagus lintneri* which is a serious pest in stored foods and on cultivated mushrooms and *Lepidoglyphus destructor* which injures Kentucky bluegrass seed in storage.

The compounds of this invention when applied by certain of the methods of this invention enter and move freely within plants, i.e., they are systemic. Thus both fungi and mites can be controlled in plants in parts well removed from the point of application. In view of this activity the compounds can be applied to seeds; thus the treatment of cucumber seeds with a few grams per 50 kilograms of seed of a compound of this invention provides control of powdery mildew (*Erysiphe cichoracearum*) and spider mites such as *Tetranychus urticae* on the resulting plants for periods in excess of 40 days. Applications to soil also provides control of certain foliage diseases and mites on plants growing in the treated soil. Spray or dust treatments of plant foliage and stems impart protection against both fungi mites to other parts of the plant not actually sprayed and to new foliage developing later. The phrase "application to the bcus to be protected" as used herein is meant to include application to plant foliage, application to seeds or application to the soil.

There are important practical advantages associated with the use of an effective systemic pesticide. Thus successful application to seed as described above, results in great savings in chemical and application costs. Soil applications which effectively protect entire plants for an extended period also represent similar savings. Distribution within the plant following foliage treatment eliminates the need not frequent retreatment to protect rapidly growing tissue. Also, materials within the plant are not subject to removal by rainfall. Similarly, movement or translocation of the chemical within the plant can provide to those parts of the plant that may not have been covered by the original spray application. This is of particular importance with plants of dense growth character resisting the intrusion of the spray and also to tall plants, such as shade trees, where the spray will not reach to the top.

An additional valuable characteristic of the compounds of this invention is their ability to prevent the spread or to kill fungus infection already established within a plant, i.e. they are curative. Thus, the compounds need not be applied until after conditions develop which permit the actual initiation of fungus attack. This means that, under some circumstances, it is possible to avoid applying any chemical during the entire life of the crop. In other cases, only a part of the normal full schedule of pesticide is required.

Therefore great savings both in chemical cost and application labor are possible with compounds capable of systemic and curative performance. Another saving is afforded by the compounds of this invention through the fact that both fungi and mites are controlled by applications of a single chemical.

The compounds of this invention provide protection from damage caused by fungi, mites or both when applied to the proper locus by the methods described hereinafter and at a sufficient rate to exert the desired fungicidal and mite ovicidal effect. The rates which will give the desired effect will be labeled, a pesticidally effective amount. They are especially suited for the protection of living plants such as fruit-bearing trees, nut-bearing trees, ornamental trees, forest trees, vegetable crops, horticultural crops (including ornamentals, small fruits and berries), fiber crops, grain and seed crops, sugarcane, sugar beets, pineapple, forage and hay crops, beans, peas, soybeans, peanuts, potatoes, sweetpotatoes, tobacco, hops, turf and pasture.

Living plants may be protected from fungi and mites by applying one or more of the compounds of this invention to the soil in which they are growing or in which they may subsequently be seeded or planted; or to seeds, tubers, bulbs or other plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solution. Preferred rates for application of the compounds of this invention to soil in which plants are or will be growing range from 0.01 to 500 parts per million by weight of the soil in which the roots are or will be growing. More preferred use rates are in the range of 0.1 to 50 parts per million, and the most preferred rates are in the range of 0.25 to 25 parts per million.

Preferred rates for application to seeds, tubers, bulbs or other plant reproductive parts, range from 0.03 to 6000 grams of active compound of this invention per 50 kilograms of planting material treated. More preferred rates are in the range of 0.3 to 3000 grams of active compound per 50 kilograms. The most preferred rates are in the range of 2.8 to 1500 grams per 50 kilograms.

Applications are made from dusts, slurries or solutions. Such treatment protect the treated parts themselves from damage due to fungi, mites, or both, and in addition, impart extended protection against both types of pests to the resulting new plants.

Preferred rates for application of the compounds of this invention to foliage, stems and fruit of living plants range from 0.012 to 60 kilograms of active ingredient per hectare. More preferred rates are in the range of 0.025 to 30 kilograms per hectare and the most preferred rates are in the range of 0.05 to 15 kilograms per hectare. The optimum amount within this range depends upon a member of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

Preferred rates for dip applications to roots of living plants are in the range of 0.5 to 18,000 grams of active ingredient per 380 liters of water or other liquid carrier. More preferred rates are in the range of 4.5 to 9,000 grams per 380 liters and the most preferred rates are in the range of 45 to 4500 grams per 380 liters.

Preferred rates for injection into the roots or stems of living plants are in the range of 0.01 to 10,000 parts per million of water or other liquid carrier. More preferred rates are in the range of 0.1 to 5,000 parts per million.

The most preferred rates are in the range of 1 to 1,000 parts per million.

Plant parts such as fruits, tubers, bulbs, foliage roots and the like, harvested for good or feed, are protected from decay and other deterioration caused by fungi or mites during processing, distribution and storage by treatment with an active compound of this invention. The plant parts to be so protected can be dipped in a liquid bath containing the active ingredient, dusted with a finely divided preparation of the active ingredient, sprayed, misted with an aerosol containing the compound, or enclosed in wrapping or packing materials impregnated with the active compound.

If a liquid bath is used, it can contain an amount of the active ingredient in the range of 1 to 5,000 parts per million of the weight of the fluid. A more preferred range for the bath is 5 to 2,500 parts per million, and the most preferred range is 10 to 1,000 parts per million.

Dusts are well as wrapping or packing materials used for this type of application can contain 0.01 to 10% of the active ingredient. More preferred rates are in the range of 0.1 to 5% and the most preferred rates are in the range of 0.2 to 2.5%.

Wood, leather, fabric, fiber board, paper and other industrial materials of an organic nature can be protected from decomposition or discoloration by fungi and infestation by mites by coating, incorporating or impregnating with an effective amount of one or more of the compounds of this invention. The coating can be accomplished by dipping, spraying, flooding, misting (as with an aerosol) or dusting the material to be protected with a suitable composition containing the active ingredient. The preferred use rates for the active ingredient in the treating preparation actually applied to the material to be protected are in the range of 0.025 to 95% by weight. More preferred rates are in the range of 0.05 to 50%, with the most preferred rates being in the range of 0.1 to 25%.

Where incorporation or impregnation procedures are to be employed, use rates may be expressed in terms of the amount of active ingredient introduced into the material to be protected. The preferred use rates for these types of applications are in the range of 0.001 to 30 percent by weight of active ingredient in the final product. More preferred rates are in the range of 0.005 to 15% with the most preferred rates being in the range of 0.01 to 7%.

Luggage, shoes, shower curtains, carpets, mats, clothing and other useful household, public or industrial items are protected from rot, fungus stains and unsightly mold growth as well as infestation by mites by the active compounds of this invention. Again, either surface or deep protection can be obtained. Surface treatment is by dips, washes, sprays, aerosols or dust applications. Deep treatment is accomplished by penetrating solutions. Sprays, dips and washes contain the active compound of the invention at rates of 10 to 5000 parts per million. Fluids for aerosol application and dusts contain 0.1 to 20% by weight. Penetrating solvent solutions contain an amount of the active ingredient that results in a deposit of 5 to 20,000 parts per million in the material to be protected.

Painted surfaces can be protected from unsightly stain and mold growth by incorporating in the paint formulation, prior to application, 5 to 20,000 parts per million of an active compound of this invention. More preferred rates are in the range of 10 to 10,000 parts per million and the most preferred rates are in the range of 20 to 5,000 parts per million. Such treatments with the compounds of this invention also protect the paint while still in the can from deterioration by fungi.

Damage by mites to stored organic products such as grain, seed, bulbs, tubers, meat or animal hides is kept to a minimum by treating the floors, walls, portions, and other parts of warehouses or other structures with one or more of the active compounds. Applications are made by the use of dusts, sprays, or aerosols with preferred use rates in the range of 0.05 to 1000 grams of the active compound of this invention per 93 square meters of surface to be kept free of excessive mite populations.

As was previously set forth, the compounds of this invention are especially suited for use on living plants. Application to the foliage, stems and fruit of plants at the rate indicated above is generally accomplished by employing sprays, dusts or aerosols containing the proper amount of active ingredient. For the control of mites and fungi which are regularly present, applications often start prior to the time that the problem actually appears and continue on a pre-determined schedule. Such a procedure is termed "preventive" or "protective".

With the compounds of this invention, successful control of plant diseases can also be accomplished by applications made after they are present. Fungus mycelia within the plant tissue are actually killed. This approach or effect is termed "curative" or "eradicant" and permits the user to realize considerable savings.

Curative control of plant diseases with the compounds of this invention is enhanced if the treated plant parts are moist for one or more periods of 2 to 12 hours each soon after the active compound is applied, Often the slow drying of an original spray treatment or naturally occuring rains, mists, fogs or dews will accomplish this. Under other circumstances, such as during dry periods or in shelters such as greenhouses, it is necessary to keep the plants moist by some special effort for best results.

When the compounds of this invention are applied, their activity can be enhanced by using certain adjuvants, for example in the water in which the fungicide is dispersed. These adjuvants may be surface-active agents, oils, humectants, enzymes, carbohydrates, and organic acids. They improve the performance on tubers, on foliage, in treatments used for dip application to roots of living plants, in liquids used for injection into the roots or stems of living plants, or in mixtures used to treat fruits, tubers, bulbs, roots and the like after harvest.

The pressures of an expanding world population, together with the need for more economical agricultural practices have resulted in earlier harvesting of grains, including corn. Frequently the grain is stored or sold to grain elevators without proper drying. Spoilage of the grain under these conditions may be quite rapid, with the formation of toxins and other substances that are very harmful or fatal when fed to animals.

Safe, effective feed additives that combat spoilage are thus of great importance to agriculture.

The compounds of this invention can be used to prevent the spoilage of animal feeds. In particular, when mixed with the feed, they provide more efficient and longer lasting protection without harm or injury to livestock that consume it. The compounds of this invention may be conveniently formulated for this use in a number of the ways previously disclosed and these formulations may be mixed directly with mixed feed, newly harvested hay and newly harvested grain. These compounds effectively prevent the spoilage of corn, sorghum, wheat, barley, oats, rye and other grains that may be used as livestock feed.

Under normal conditions, these compounds may be incorporated into feeds at rates of from 0.01% to 0.25% with excellent results. Higher rates may be required under very damp conditions.

COMPOSITIONS

Compositions of this invention are formulated by mixing a compound of this invention with one or more agricultural adjuvants, e.g. surface active agents.

The surface active agents used in this invention can be wetting, dispersing or emulsifying agents. They may act as wetting agents for wettable powders and dusts, as dispersing agents for wettable powders and suspensions and as emulsifying agents for emulsifiable concentrates. Surfactants also enhance the biological activity of the compounds of this invention. Such surface active agents can include such anionic, cationic and nonionic agents as have heretofore been generally employed in plant control compositions of similar type. Suitable surface active agents are set out, for example, in "Detergents and Emulsifiers Annual - 1969" by John W. McCutcheon, Inc. Other surface active agents not listed by McCutcheon but still effective dispersants by virtue of protective colloid action include methyl cellulose, polyvinyl alcohol, hydroxyethyl-cellulose, and alkyl substituted polyvinyl pyrrolidones.

Suitable surface active agents for use in compositions of this invention include polyethylene glycol esters with fatty and rosin acids, polyethylene glycol ethers with alkyl phenols or with long-chain aliphatic alcohols, polyethylene glycol ethers with sorbitan fatty acid esters, and polyoxyethylenethio ethers. Other suitable surfactants include amine, alkali and alkaline earth salts of alkylaryl sulfonic acids; amine, alkali and alkaline earth fatty alcohol sulfates; dialkyl esters of alkali metal sulfosuccinates; fatty acid esters of amine, alkali and alkaline earth isethionates and taurates; amine, alkali and alkaline earth salts of lignin sulfonic acids; methylated or hydroxyethylated cellulose; polyvinyl alcohols; alkyl substituted polyvinyl pyrrolidone; amine, alkali and alkaline earth salts of polymerized alkylnaphthalene sulfonic acids; and long-chain quaternary ammonium compounds. Anionic and nonionic surface active agents are preferred.

Among preferred wetting agents are sodium alkylnaphthalene sulfonates, sodium dioctylsulfosuccinate, sodium dodecylbenzene sulfonate, ethylene oxide condensates with alkylated phenols such as octyl, nonyl and dodecyl phenol, sodium lauryl sulfate and trimethylnonyl polyethylene glycols. Among preferred dispersing agents are sodium, calcium and magnesium lignin sulfonates, low-viscosity methyl cellulose, low-viscosity polyvinyl alcohol, alkylated polyvinylpyrrolidone, polymerized alkyl naphthalene sulfonates, sodium N-oleyl or N-lauryl isethionates, sodium N-methyl-N-palmitoyl taurate and dodecylphenol polyethylene glycol esters.

Among preferred emulsifying agents are ethylene oxide adducts of lauric, oleic, palmitic or stearic acid esters of sorbitan or sorbitol; polyethylene glycol esters with lauric, oleic, palmitic, stearic or rosin acids; oil-soluble alkylarylsulfonates; oil-soluble polyoxyethylene esters with octyl, nonyl and dodecylphenol; polyoxyethylene adducts to long-chain mercaptans; and mixtures of these surfactants.

In general, less than 10% by weight of the surface-active agent will be used in compositions of this invention and ordinarily the amount of surface-active agents will range from 1-5% but may even be less than 1% by weight.

Additional surface-active agents can be added to the above formulation to increase the ratio of surface-active agent: active agent up to as high as 5:1 by weight. Normally the purpose of adding higher amounts of surfactant is to increase the fungicidal effect of the active compounds. When used at higher rates it is preferred that the surfactant is present in the range of one-fifth to five parts surfactant for each one part of active agent.

Compositions of this invention will contain addition to surface active agents other agricultural adjuvants such as solid or liquid diluents to produce wettable powders, dusts, granules or emulsifiable liquids as desired.

A. Wettable Powders

Wettable powders are compositions which usually contain inert solid diluents in addition to surfactants. These inert diluents may serve several purposes. They can act as grinding aids to prevent mill smear and screen blinding, they can aid rapid dispersion of the mix when placed in water, they can adsorb liquid or low melting solid active material to produce a free flowing solid product, they can prevent agglomeration into lumps upon prolonged hot storage and they can permit preparation of compositions with a controlled amount of active ingredient so that proper dosage is easily measured by the consumer.

Suitable diluents may be either inorganic or organic in origin. These include the natural clays, diatomaceous earth, synthetic mineral fillers derived from silica or silicates, insoluble salts produced by precipitation in flurry form such as triacalcium phosphate or calcium carbonate, and powdered organic diluents such as shell flours, wood flours, corn cob flour or sucrose. Preferred fillers for the compositions of this invention include kaolin clays, attapulgite clay, nonswelling calcium magnesium montmorillonites, synthetic silicas, synthetic calcium and magnesium silicates, diatomaceous silica, corn cob flour and sucrose.

Wettable powders will normally contain both a wetter and a dispersant. Most preferred for dry wettable powders are those anionic and nonionic surfactants which exist in solid form. Occasionally a liquid, nonionic surfactant, normally considered an emulsifying agent can be used to produce both wetting and dispersion.

Wetting and dispersing agents in wettable powders of this invention, when taken together, will comprise from about 0.5 weight percent to 5.0 weight percent of the total composition. The active component will be present at a concentration of from about 25% to 80% and diluent makes up the balance to 100%. Where needed a corrosion inhibitor or foaming inhibitor may be added at rates of 0.1% to 1.0% with a corresponding reduction in diluent.

B. Dusts

Dust compositions are those intended for application in dry form with suitable dusting equipment. Since wind drift is undersirable when applying dusts, the most suitable dust diluents are those which are dense and rapid settling. These include kaolinites, talcs, pyrophyllites, ground phosphate rock, Serecite, and ground tobacco stems. However, dusts are usually most easily prepared by diluting an existing high-strength wettable powder with a diluent so that the final dust will frequently contain a fraction of light, absorptive diluent as well as a denser filler.

A wetting agent is desirable in dust formulations so that adhesion to dew-covered foliage is enhanced. Dusts made from wettable powders will usually contain sufficient wetter, but dusts made directly from unformulated active will usually contain an added wetting agent. Dry solid anionic or nonionic wetters are preferred.

Dust formulations will normally contain from 5.0 weight percent to 25 weight percent of active material, from 0.005% to 1.0% wetting agent, and from 3% to 20% light grinding aid diluent and the balance dense, rapid settling diluents. If made by diluting a prepared wettable powder it will also contain a small amount of dispersing agent which has no active role when the composition is used as a dry dust.

C Emulsifiable Liquids

Emulsifiable liquids are formulated by combining the compounds of this invention with a suitable emulsifier and an organic liquid with low water solubility. The active component may be completely dissolved in the organic liquid or it may be a finely ground suspension in a nonsolvent liquid. Suitable organic liquids include alkylated naphthalenes, xylene, high molecular weight ketones, such as isophorones, dibutyl or diamyl ketone, esters such as amyl acetate and normal or iso paraffins. Most preferred emulsifiers are blends of oil soluble sulfonates and nonionic polyoxyethylene glycol esters or ethers of fatty acids or alkylated phenols.

The active component in emulsifiable concentrates will be present at from 10 weight percent to about 40 weight per cent. Combined emulsifiers will be present at from 3 weight percent to about 10 weight percent and the balance will be an organic carrier liquid or solvent.

D. Granules

Soil treatments with fungicides, either pre- or post-emergence can frequently be most readily applied with granules. Granular products, with the compounds of this invention, can be made in a number of ways. The active materials can be melted or dissolved in a volatile carrier and sprayed upon preformed granules. They may be mixed as powders with suitable diluents and binders, then moistened and granulated followed by drying. Powders may also be applied to coarsely porous granules by tumbling together and applying some non-volatile liquid such as oil, glycol or a liquid non-ionic surfactant to act as a binder. Rates of granule disintegration and dispersion of active material in moist soil can be controlled by choice of added surfactants or selection of the binder used to form the granule.

Suitable preformed granules include those made from attapulgite clay, granular expanded vermiculite, ground corn cobs, ground nut shells or preformed kaolinite granules. When active fungicide is placed upon such carriers the concentration may range from 1% to 25%. However, unless applied from a molten state, it is difficult to prevent segregation of active and carrier in concentration ranges above about 10% on preformed granules. When higher concentrations of active are desired best results are obtained by premixing powdered active, diluents, binders and surfactants, then granulating so that the active is distributed throughout the granule and not solely upon its surface.

Suitable diluents for the preparation of granules by granulation or extrusion include kaolin clays, sucrose, non-swelling calcium-magnesium montmorillonites, and gypsum. Cohesion to a firm granule is usually obtained by moistening, compacting and drying, with or without some binding agent. Kaolin clays form firm granules if bound together with gelatinous agents such as methylcellulose, natural gums or swelling bentonite. Ca, Mg bentonites require no binder and gypsum can be made to form firm granules with either the addition of plaster of Paris or certain salts such as ammonium sulfate, potassium sulfate or urea which form double salts with gypsum.

The active content of formed granules can range from 1–90% although 75% active represents about the upper level if controlled disintegration of the granule in moist soil is desired. Control of disintegration rate is attained by controlled compaction, e.g., controlled extrusion pressure or by the addition of inert water-soluble components such as sodium sulfate or sugar which can leach away.

E. Aqueous Dispersions

Aqueous dispersions of fungicides may be preferred to wettable powders where minimum agitation is available in application equipment and accurate dosage is essential. Even the best and finest wettable powder will not disperse completely in water. Small agglomerates remain which settle rapidly. However, when a solid is ground in a water phase, in the presence of dissolved surfactants, each particle develops an adsorbed layer that repels its neighbors and complete dispersion is maintained. This will still not prevent a slow settling to the bottom of stored containers with the formation of a dense "clay" that is difficult to resuspend. A practical aqueous dispersion concentrate must be free from "claying" during an extended shelf life. Certain acrylic acid polymers and sheared hydrated attapulgite will effectively prevent claying.

Suitable aqueous dispersions of the compounds of this invention are prepared by pebble milling or sand milling the active ingredient, one or more dispersants and an anticlaying component in water until the active particle size is less than 10 microns, preferably less than 5 microns. In climates where freezing is a problem, mixtures of glycols and water may be used as the continuous phase.

F. Solutions

Solutions of active ingredient, when available, may also be preferable to other formulations intended for application in liquid form. Alkali metal salts of the active compounds of this invention can be dissolved in polar solvents to give solutions which may be used with minor dilution in ultra low volume or low volume applications or which may be diluted with water to give solutions or dispersions for conventional application.

G. Low Volume Applications

While conventional applications of sprayable formulations have usually been made in a dilute form (for example at a ratio of about 200 liters per hectare or more), the compounds of this invention can also be applied at higher concentrations in the typical "ultra-low-volume" or "low-volume" applications from aircraft or ground sprayers. For this purpose wettable powders can be dispersed in small amounts of aqueous or non-aqueous carriers and the suspension for emulsifiable concentrates can be used directly or with minor dilution. Special compositions, particularly suitable for ULV applications and solutions or finely divided suspensions in one or more carriers such as dialkylformamides, N-alkylpyrrolidones, dimethylsulfoxide, water esters, ketones, glycols, glycol ethers and the like. Other suitable carriers include aromatic hydrocarbons (halogenated and non-halogenated), aliphatic hydrocarbons (halogenated and non-halogenated) and the like.

The compositions of the invention can contain, in addition to the active ingredient of this invention, conventional insecticides, miticides, bactericides, nematocides, fungicides, or other agricultural chemicals such as fruit set agents, fruit thinning compounds, fertilizer ingredients and the like, so that the compositions can serve useful purpose in addition to the control of fungi and mite infestations.

The following are illustrative of the agricultural chemicals that can be included in the conpositions or, additionally, that may be added to sprays containing one or more of the active compounds.

The additional agricultural chemicals are employed in mixtures or combinations in amounts ranging from one-fifth to twenty times that of the compound or compounds of this invention. The proper choice of amounts is readily made by one skilled in the art of protecting plants from pest depredations.

1,2,3,4,10,10-hexachloro-1,4,4a,5,8,8a-hexahydro-1,4-endoexo-5,8-dimethanonaphthalene (aldrin);
1,2,3,4,5,6-hexachlorocyclohexane (lindane);
2,3,4,5,6,7,8,8-octachloro-4,7-methano-3a-4,7,7atetrahydroindane;
1,1,1-trichloro-2,2-bis(p-chlorophenyl)ethane (DDT);
1,2,3,4,10,10-hexachloro-6,7-epoxy-1,4,4a-5,6,7,8,8a-octahydro-1,4-endo-exo-5,8-dimethanonaphthalene (dieldrin);
1,2,3,4,10,10-hexachloro-6,7-epoxy-1,4,4a,5,6,7,8-,8a-octahydro-1,4-endo-endo-5,6-dimethanonaphthalene (endrin);
1 (or 3a), 4,5,6,6,8,8-heptachloro-3a-4,7,7a-tetrahydro-4,7-methanoindene;
1,1,1-trichloro-2,2-bis(p-methoxyphenyl)ethane (methoxychlor);
1,1-dichloro-2,2-dichloro-2,2-bis(p-chlorophenyl)ethane;
chlorinated camphene having a chlorine content of 67-69%
2-nitro-1,1-bis(p-chlorophenyl)butane;
1-naphthyl-N-methylcarbamate ("Sevin");
methylcarbamic acid, ester with phenol, 4-(dimethylamino)-3,5-dimethyl;
methylcarbamic acid, ester wth 1,3-dithiolan-2-one oxime;
O,O-diethyl-O-(2-isopropyl-4-methylpyrimid-6-yl) thiophosphate,
O,O-dimethyl-1-hydroxy-2,2,2-trichloroethyl phosphonate;
O,O-dimethyl-S-(1,2-dicarbethoxyethyl)dithiophosphate (malathion);
O,O-dimethyl-O-p-nitrophenyl thiophosphate (methyl parathion);
O,O-dimethyl-O-(3-chloro-4-nitrophenyl)thiophosphate;
O,O-diethyl-O-p-nitrophenyl thiophosphate (parathion);
dl-2-cyclopentenyl-4-hydroxy-3-methyl-2-cyclopenten-1-one chrysanthemate;
O,O-dimethyl-O-(2,2-dichorovinyl)phosphate (DDVP); mixture containing 53.3% "Bulan", 26.7% "Prolan" and 20.0% related compounds;
O,O-dimethyl-O-(2,4,5-trichlorophenyl)phosphorothioate;
O,O-dimethyl-S-(4-oxo-1,2,3-benzotriazine-3(4H)-yl-methyl)-phosphorodithioate ("Guthion");
bis(dimethylamino)phosphonous anhydride;
O,O-diethyl-O-(2-keto-4-methyl-7-a'-pyranyl)thiophosphate;
O,O-diethyl (S-ethyl mercaptomethyl)dithiophosphate;
calcium arsenate;
sodium aluminofluoride;
dibasic lead arsenate;
2'-chloroethyl-1-methyl-2-(p-tert-butylphenoxy)ethyl sulfite; azobenzene;
ethyl 2-hydroxy-2,2-bis(4-chlorophenyl)acetate;
O,O-diethyl-O-(2-(ethylmercapto)-ethyl)thiophosphate;
2,4-dinitro-6-sec-butyl phenol; toxaphene;
O-ethyl-O-p-nitrophenylbenzenethiophosphonate;
4-chlorophenyl-4-chlorobenzene sulfonate;
p-chlorophenyl-phenyl sulfone;
tetraethyl pyrophosphate;
1,1-bis(p-chlorophenyl)ethanol;
1,1-bis(chlorophenyl)-2,2,2-trichloroethanol;
p-chlorophenyl-p-chlorobenzyl sulfide;
bis(p-chlorophenoxy)methane;
3-(1-methyl-2-pyrrolidyl)pyridine;
mixed ester of pyrethrolone and cinerolone keto-alcohols and two chrysanthemum acids;
cube and derris, both whole root and powdered; ryanodine;
mixture of alkaloids known as veratrine;
dl-2-allyl-4-hydroxy-3-methyl-2-cyclopenten-1-one esterified with a mixture of cis and trans dl-chrysanthemum monocarboxylic acids;
butoxypolypropylene glycol;
p-dichlorobenzene;
2-butoxy-2'-thiocyanodiethyl ether;
naphthalene;
methyl O-carbamylthiolacetohydroxamate;
1,1-dichloro-2,2-bis(p-ethylphenyl)ethane;
methyl O-(methylcarbamoyl)thiolacetohydroxamate;
p-dimethylaminobenzenediazo sodium sulfonate;
quinone oxyaminobenzooxohydrazone;
tetraalkyl thiuram disulfides such as tetramethyl thiuram disulfide or tetraethyl thiuram disulfide; sulfur;
metal salts of ethylene bisdithiocarbamic acid, e.g. manganese, zinc, iron and sodium salts;
pentachloronitrobenzene;
N-dodecylguanidine acetate (dodine);
N-trichloromethylthiotetrahydrophthalimide (captan);
phenylmercury acetate;
2,4-dichloro-6-(o-chloroaniline)-s-triazine ("Dyrene");

N-methylmercury p-toluenesulfonilide;
chlorophenolmercury hydroxides;
nitrophenolmercury hydroxides;
ethylmercury acetate;
ethylmercury 2,3-dihydroxypropyl mercaptide;
methylmercury acetate;
methylmercury 2,3-dihydroxypropyl mercaptide;
3,3'-ethylenebis(tetrahydro-4,6-dimethyl-2H-1,3,5-thiodiazine-2-thione);
methylmercury dicyandiamide;
N-ethylmercury-p-toluenesulfonilide;
1,4-dichloro-2,5-dimethoxy benzene;
metal (e.g. iron, sodium and zinc), ammonium and amine salts of dialkyl dithiocarbamic acids;
tetrachloronitroanisole;
hexachlorobenzene;
hexachlorophene;
methylmercury nitrile;
tetrachloroquinine;
N-trichloromethylthiophthalimide;
1,2-dibromo-3-chloropene;
1,2-dibromo- 3-chloroprene;
dichloropropane - dichloropropene mixture;
ethylene dibromide;
chloropicrin;
sodium dimethyl dithiocarbamate;
tetrachloroisophthalonitrile;
1-benzimidazole carboxylic acid, 2-carboxyamino-dimethyl ester streptomycin;
2-(2,4,5-trichlorophenoxy)propionic acid;
p-chlorophenoxyacetic acid;
1-naphthaleneacetamide; and
N-(1-naphthyl)acetamide.

The agricultural chemicals listed above are merely exemplary of the compounds which can be mixed with the active compounds and are not intended to any way limit the invention.

The use of pesticides such as those listed above in combination with a compound within the scope of this invention sometimes appears to greatly enhance the activity of the active compound. In other words, an unexpected degree of activity is sometimes seen when another pesticide is used along with the active compound.

In order that the invention may be better understood, the following examples are given in addition to those above. All parts are parts by weight otherwise indicated.

Wettable Powders

EXAMPLE 11

| | Percent |
|---|---|
| Methyl 4-[o-(2,4-dichlorobenzylideneamino)-phenyl]-3-thioallophanate | 50 |
| alkylnaphthalenesulfonic acid, sodium salt | 1 |
| low viscosity methyl cellulose | 0.5 |
| Kaolin clay | 48.5 |

The ingredients are combined, mixed, micropulverized, air milled and then blended. The resulting powder wets and disperses readily in water and is suitable for application in normal spray equipment. Any of the other tnioallophanates mentioned above may be substituted for the active ingredient here to give useful wettable powders.

The above 50% wettable powder formulation is dispersed in water to give an active ingredient concentration of 300 ppm in water. Eight uniform apple trees of the same variety are selected for testing. Four of these are sprayed to run-off, which is approximately 2850 liters per hectare, at weekly intervals during the growing season with the above formulation, and the other four trees are left unsprayed.

By the end of the season the unsprayed trees are highly infected with apple scab, *Venturia inaequalis*, and have poor twig growth and small, spotted fruit. The trees sprayed with the formulation of this example are essentially free of apple scab disease, have foliage of a thrifty, dark green color, and exhibit good twig growth and fruit size.

EXAMPLE 12

| | Percent |
|---|---|
| Methyl 4-[o-(4-methylbenzylideneamino)phenyl]-3-thio-allophanate | 60 |
| dialkylsulfosuccinate, sodium salt | 1 |
| sodium ligninsulfonate | 1 |
| diatomaceous silica | 38 |

The materials are combined, air milled twice, and then blended.

The formulation of this example is useful for the control of peach scab and brown rot caused by the fungi, *Cladosporium carpophilum* and *Monolimia laxa*. This is demonstrated by an orchard study in which random trees in a peach planting are sprayed to run off. Starting in the spring selected trees are sprayed from all sides with the formulation of this example at a rate of 300 ppm active ingredient in water. The same trees are sprayed each 14 days throughout the season. At harvest the trees receiving the treatment are heavily laden with large healthy peaches. On the other hand, the trees which did not receive the treatment had only a few fruit because of a severe blossom blight infection with brown rot, and those remaining fruit were severely spotted with scab lesions.

EXAMPLE 13

| | Percent |
|---|---|
| Methyl 4-[o-(2-bromobenzylideneamino)phenyl]-3-thio-allophanate | 50 |
| alkylbenzenesulfonic acid, sodium salt | 1 |
| sodium ligninsulfonate | 1 |
| diatomaceous silica | 48 |

The materials are combined, micropulverized, air milled, and then blended.

A uniform field planting of cantaloupe in North Carolina is inoculated with the powdery mildew fungus (*Erysiphe cichoracearum*). *After* 10 days this organism has become well established in the plants.

At this time alternate rows are sprayed with water containing a suspension of the wettable powder prepared as described above and an added amount of a polyhydric alcohol ester surface-active agent ("Trem" 014). The concentrations of this chemical suspension is such as to give 227 grams of the active compound of this formulation per 378 liters of water (600 ppm) and 400 ppm of the surfactant. The spray is applied at a volume of 1400 liters per hectare. The remaining rows are left unsprayed.

After another 15 days the unsprayed rows are heavily damaged by powdery mildew and some of the plants are dying. The sprayed rows, however, are healthy and growing rapidly. The results indicate that the active compound of the suspension acts as a curvative fungicide.

EXAMPLE 14

| | Percent |
|---|---|
| Methyl 4-[o-(4-methoxybenzylideneamino)phenyl]-3-thioallophanate | 50 |
| sucrose + impurities in technical active material | 46.5 |
| dioctylsulfosuccinate, sodium salt | 3 |
| low viscosity methyl cellulose | 0.5 |

The materials are combined, micropulverized, air milled and then blended.

Test plots are established in a rice field. The plots are sprayed with water containing a suspension of the wettable powder described above along with a polyhydric alcohol ester surface active agent ("Trem" 014). The amount of the wettable powder used is such as to provide 0.6 grams of the active compound of this invention per liter of water (600 ppm). The amount of "Trem" 014 is 400 ppm in the final spray. The spray is applied at weekly intervals at the rate of 900 liters per hectare. The remainder of the field is left unsprayed. Three months after the start of the test, the sprayed plots are healthy and growing well. The untreated plots, on the other hand, are seriously damaged by the rice blast fungus, *Piricularia oryzae which greatly reduces yield.*

The following compounds are each substituted one at a time for the methyl 4-[o-(4-methoxybenzylideneamino)phenyl]-3-thioallophanate above in like amount by weight. When formulated and applied in like manner, like results are obtained.

Methyl 4[o-(o-fluorobenzylideneamino)phenyl]-3-thioallophanate

Methyl 4-[o-(2,4-dichlorobenzylideneamino)-phenyl]-3-thioallophanate

Methyl 4-[o-(o-chlorobenzylideneamino)phenyl]-3-thioallophanate

Methyl 4-(o-benzylideneaminophenyl)-3-thioallophanate

Methyl 4-[o-(3-nitrobenzylideneamino)phenyl]-3-thioallophanate

Methyl 4-[o-(4-methylbenzylideneamino)phenyl]-3-thioallophanate

Methyl 4[o-(2-bromobenzylideneamino)phenyl]-3-thioallophanate

Dusts

EXAMPLE 15

| | Percent |
|---|---|
| Methyl 4-[o-(o-fluorobenzylideneamino)phenyl]-3-thioallophanate | 5 |
| Kaolin | 5 |
| Sodium dialkylsulfosuccinate | 0.5 |
| Talc | 89.5 |

The active material, surfactant and kaolin are combined and ground and then mixed with the talc and blended.

A single row is selected in a sugar beet field for treatment with the dust of this formulation. After the sugar beets are one month old and a few lesions of *Carcospora beticola* have become evident as spots on the leaves, weekly dust treatments are applied to the selected row. The 5% dust of this formulation is applied to a single row at approximately 30 kilograms per hectare. There is some drift to adjacent rows but the remainder of the field is left untreated. At harvest the foilage is examined and the beets are dug and weighed. The treated row is a vigorous healthy row with lush green foliage and the beets are large and normal. The adjacent rows are spotted with numerous leaf spot lesions and the remainder of the field is almost entirely defoliated. A few young leaves on the untreated beets are still green but all of the older leaves are dried up. Beets from the untreated rows are less than half normal size.

Any of the compounds of this invention can be formulated in like manner and applied with similar results.

EXAMPLE 16

| | Percent |
|---|---|
| Methyl 4-[o-(2,4-dichlorobenzylideneamino)phenyl]-3-thioallophanate | 50 |
| alkylnaphthalenesulfonic acid, sodium salt | 1 |
| low viscosity methyl cellulose | 0.5 |
| Kaolin clay | 48.5 |

The ingredients are combined, mixed, micropulverized, air milled and then blended. The resulting powder wets and disperses readily in water and is suitable for application in normal spray equipment. Any of the other thioallophanates mentioned above may be substituted for the active ingredient here to give useful wettable powders.

The above 50% wettable powder formulation is dispersed in water to give an active ingredient concentration of 2000 ppm in water. Eight uniform apple trees of the same variety are selected for testing. Four of these are sprayed to run-off, which is approximately 2850 liters per hectare, at weekly intervals during the growing season with the above formulation, and the other four trees are left unsprayed.

By the end of the season the unsprayed trees have developed very high populations of orchard mites and are highly infected with apple scab, *Venturia inaequalis*. Due to the feeding of the mites, the foliage is russeted and drops prematurely. Also the untreated trees have poor twig growth and small, spotted fruit. The trees sprayed with the formulation of this example are essentially free of mites, their eggs and apple scab disease. As a result of the excellent mite control, the sprayed trees have foliage of a thrifty, dark green color, and they exhibit good twig growth and fruit size.

Dusts

EXAMPLE 17

| | Percent |
|---|---|
| Wettable powder of Example 11 | 6 |
| Micaceous talc | 94 |

The above components are blended to give a freely flowing dust.

This dust formulation is applied to individual vines of grapes in otherwise untreated rows in a vineyard. The applications are made at a rate of 20 kilograms per hectare at 14-day intervals for a period of three months during the growing season. At the end of the treatment period the treated vines are healthy, support a heavy crop of high quality fruit, and show evidence of excellent cane growth. The foliage and fruit of untreated vines are severely damaged by powdery mildew (*Uncinula necator*) and by *Botrytis* and other fruit rots.

Any of the wettable powders of Examples 11-14 inclusive may be formulated and applied in like manner with similar results.

Granules

EXAMPLE 18

| | Percent |
|---|---|
| Methyl 4-[o-(benzylideneamino)phenyl]-3-thioallophanate | 20 |
| Attapulgite clay | 6 |
| Calcium, magnesium bentonite | 66 |
| Sodium sulfate, anhydrous | 8 |

The powdered active material is combined with the other ingredients and moist granulated, dried and then screened to make a 20–80 mesh mixture.

A field in California is seeded with cotton in the normal manner, except that granules prepared as set forth above are added to alternate rows. These granules are dropped in such a way that some fall into the furrow and some are mixed with the covering soil. The rate of granule application is such as to employ 2.0 kilograms of active chemical of this invention per 3600 meters of row. The remaining rows are untreated.

Six weeks after planting, many of the plants in the rows without the granules are dead, and others show soreshin lesions caused by *Rhizoctonia solani.*

Pellets

EXAMPLE 19

| | Percent |
|---|---|
| Methyl 4-[o-(4-methoxybenzylideneamino)phenyl]-3-thioallophanate | 25 |
| calcium, magnesium bentonite | 64 |
| sodium sulfate, anhydrous | 10 |
| alkylnaphthalenesulfonic acid, sodium salt | 1 |

This composition is blended, moistened with water in a pug mill and then extruded and dried.

The pellets of this example may be applied in a manner similar to the granules of Example 18 with comparable results.

EXAMPLE 20

| | Percent |
|---|---|
| Methyl 4-[o-(o-fluorobenzylideneamino)phenyl]-3-thioallophanate | 30 |
| calcium, magnesium ligninsulfonate (goulac) | 15 |
| attapulgite, hydrated | 3 |
| disodium phosphate, anhydrous | 1 |
| dodecyl alcohol | 0.005 |
| water | 50.995 |

The dispersion is prepared by mixing the ingredients and sandmilling the mixture.

Six field crates of oranges are picked from a commercial grove in Florida. Three of these crates of oranges are dipped for 3 minutes in a water bath containing a suspension made from the above formulation, in an amount to give 300 parts per million by weight of the active ingredient of this invention. A polyethylene glycol ester of oleic acid surface active agent is present at the rate of 150 ppm of total liquid. The remaining three crates are dipped in a similar fashion in water with the surface-active agent only. All crates are set aside in a citrus storage house for three weeks. At the end of this time all fruits are examined. The fruit that has been dip-treated with the compounds of this invention is still in good condition, but the fruit that is not so protected is largely rotted by the blue mold fungus (*Penicillium digitatum*).

The other compounds of this invention may be similarly formulated and when used as above give like results.

Oil Dispersion

EXAMPLE 21

| | Percent |
|---|---|
| Methyl 4-[o-(4-methoxybenzylideneamino)phenyl]-3-thioallophanate | 25 |
| blend of polyalcohol carboxylic acid esters and sulfonated oils | 8 |
| isoparaffin oils (Soltrol 170) | 67 |

The dispersion is prepared by mixing the ingredients and sandmilling the mixture. The resulting dispersion can be sprayed as a concentrate, diluted with oil or emulsified in water and the applied.

The formulation of this example is useful for the control of the Sigatoka disease fungus (*Mycosphaerella musicola*). This is demonstrated by a plantation study in which a plot showing the first visable yellow spots of the disease is sprayed from the air with an aqueous suspension of this formulation containing 454 grams of active ingredient in 45 liters of water per hectare. The adjacent plots, also showing signs of incipient disease, are left untreated. At harvest the foliage is examined and representative samples of fruit weighed. The untreated plots show severely damaged leaves and prematurely ripened, small, unmarketable bananas. The treated plot yields heavy well developted bananas from vigorous undiseased plants.

The following compounds may be substituted one at a time for the methyl 4-[o-(4-methoxybenzylideneamino)phenyl]-3-thioallophanate above in like amount by weight. When formulated and applied in like manner, like results are obtained.

Methyl 4-[o-(o-fluorobenzylideneamino)phenyl]-3-thioallophanate

Methyl 4-[o-(2,4-dichlorobenzylideneamino)-phenyl]-3-thioallophanate

Methyl 4-[o-(o-chlorobenzylideneamino)phenyl]-3-thioallophanate

Methyl 4-(o-benzylideneaminophenyl)-3-thioallophanate

Methyl 4[o-(3-nitrobenzylideneamino)phenyl]-3-thioallophanate

Methyl 4-[o-(4-methylbenzylideneamino)phenyl]-3-thioallophanate

Methyl 4-[o-(2-bromobenzylideneamino)phenyl]-3-thioallophanate

Solution

EXAMPLE 22

| | Percent |
|---|---|
| Methyl 4-[o-(4-methylbenzylideneamino)phenyl]-3-thioallophanate | 10 |
| LiOH . $H_2O$ | 1.5 |
| Methanol | 40 |
| Ethylene glycol | 48.5 |

The active ingredient, lithium hydroxide, and methanol are stirred together until a homogeneous solution results; this solution is then mixed with the glycol.

A single row is selected in a sugar beet field for treatment with the solution of this formulation. After the sugar beets are one month old and several lesions of *Cercospora beticola* have become evident as spots on the leaves, weekly treatments are applied to the selected row. The 10% solution of this formulation is applied to a single row at approximately 200 grams of the active ingredient per hectare. There is some drift to adjacent rows but the remainder of the field is left untreated. At harvest the foliage is examined and the beets are dug and weighed. The treated row is a vigorous healthy row with lush green foliage and the beets are large and normal, clearly demonstrating the eradicant nature of this treatment. The adjacent rows are spotted with numerous leaf spot lesions and the remainder of the field is almost entirely defoliated. A few young leaves on the untreated beets are still green but all of the older leaves are dried up. Beets from the untreated rows are less than half normal size.

I claim:

1. A method of preventing injury due to mites or fungi comprising applying to the locus to be protected from fungi and mites a pesticidally effective amount of a compound of the formula:

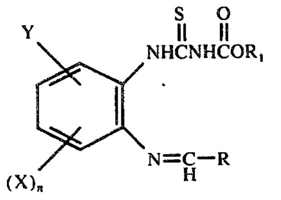

wherein

X is hydrogen, fluorine, chlorine, or bromine;

Y is hydrogen or alkyl of 1 to 4 carbon atoms;

$R_1$ is alkyl of 1 to 12 carbon atoms;

R is thienyl; furyl; naphthyl; pyridyl; quinolyl; alkyl of 1 to 12 carbon atoms; alkoxy of 1 to 3 carbon atoms or

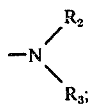

$R_2$ is hydrogen or alkyl of 1 to 4 carbon atoms;

$R_3$ is alkyl of 1 to 4 carbon atoms, provided that $R_2$ and $R_3$ can be taken together and be $-CH_2CH_2OCH_2CH_2-$ or $-(CH_2)_m-$; when Y is alkyl, *n* is O; when Y is hydrogen, *n* is 1, 2 or 3; *m* is 4 to 6; and the sodium, potassium, lithium, calcium, barium, copper, zinc and manganese salts of these compounds.

2. A method of claim 1 wherein X and Y are hydrogen and $R_1$ is methyl, ethyl or isopropyl.

3. The method of claim 1 in which the compound is methyl 4-[o-(2-furfurylideneamino)phenyl]-3-thioallophanate.

4. The method of claim 1 in which the compound is methyl 4-[o-(2-pyridylmethyleneamino)phenyl]-3-thioallophanate.

5. The method of claim 1 in which the compound is methyl 4-[o-(2-quinolylmethyleneamino)phenyl]-3-thioallophanate.

6. The method of claim 1 in which the compound is methyl 4-[o-(2,2-dimethylpropylideneamino)phenyl]-3-thioalophanate.

7. The method of claim 1 in which the compound is methyl 4-[o-methoxymethyleneaminophenyl]-3-thioallophanate.

8. A fungicidal composition comprising a suitable agricultural adjuvant and a fungicidally effective amount of a compound of the formula

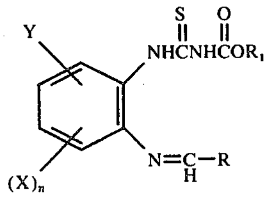

wherein

X is hydrogen, fluorine, chlorine, or bromine;

Y is hydrogen or alkyl of 1 to 4 carbon atoms; $R_1$ is thienyl; furyl; naphthyl; pyridyl; quinolyl; alkyl of 1 to 12 carbon atoms; alkoxy of 1 to 3 carbon atoms or

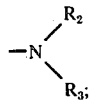

$R_2$ is hydrogen or alkyl of 1 to 4 carbon atoms;

$R_3$ is alkyl of 1 to 4 carbon atoms, provided that $R_2$ and $R_3$ can be taken together and be $-CH_2CH_2OCH_2CH_2-$ or $-(CH_2)_m-$; when Y is alkyl, *n* is O; when Y is hydrogen, *n* is 1, 2 or 3; *m* is 4 to 6; and the sodium, potassium, lithium, calcium, barium, copper, zinc and manganese salts of these compounds.

9. A composition of claim 8 wherein X and Y are hydrogen and $R_1$ is methyl, ethyl or isopropyl.

10. A composition of claim 8 wherein the compound is methyl 4-[o-(2-furfurylideneamino)phenyl]-3-thioallophanate.

11. A composition of claim 8 wherein the compound is methyl 4-[o-(2-pyridylmethyleneamino)phenyl]-3-thioallophanate.

12. A composition of claim 8 wherein the compound is methyl 4-[o-(2-quinolylmethyleneamino)phenyl]-3-thioallophanate.

13. A composition of claim 8 wherein the compound is methyl 4-[o-(2,2-dimethylpropylideneamino)-phenyl]-3-thioallophanate.

14. A composition of claim 8 wherein the compound is methyl 4-[o-methoxymethylene aminophenyl]-3-thioallophanate.

* * * * *